United States Patent [19]

Musoke et al.

[11] Patent Number: 5,273,744
[45] Date of Patent: Dec. 28, 1993

[54] VACCINES FOR THE PROTECTION OF ANIMALS AGAINST THEILERIA INFECTION

[75] Inventors: Anthony J. Musoke, Kampala, Uganda; Vish Nene, Cambridge, England; Keith Iams, Pittsburgh, Pa.; Vinand M. Nantulya, Mbale, Uganda

[73] Assignee: International Laboratory for Research on Animal Diseases, Nairobi, Kenya

[21] Appl. No.: 835,043

[22] Filed: Feb. 11, 1992

Related U.S. Application Data

[63] Continuation of Ser. No. 365,999, Jun. 14, 1989, abandoned.

[51] Int. Cl.5 ............................................. A61K 39/00
[52] U.S. Cl. ..................................... 424/88; 530/350; 530/395; 530/806; 435/69.3
[58] Field of Search ............... 530/395, 350, 806; 424/88; 435/69.3

[56] References Cited

U.S. PATENT DOCUMENTS

| | | | |
|---|---|---|---|
| 4,020,151 | 4/1977 | Bolz et al. | 436/527 |
| 4,394,443 | 7/1983 | Weissman et al. | 435/6 |
| 4,713,366 | 12/1987 | Stevens | 514/13 |
| 4,835,260 | 3/1989 | Shoemaker | 530/397 |
| 5,006,334 | 4/1991 | Stevens | 424/88 |

OTHER PUBLICATIONS

Williamson, S., et al., "Theileria annulata sporozoite surface antigen expressed in *Escherichia coli* elicits neutralizing antibody," *Proc. Natl. Acad. Sci. USA*, 86:4639-4643 (Jun. 1989).

Scoper, R. K. 1987, *Protein Purification*, Springer-Verlag, New York, pp. 167-172.

Aebersold et al. 1986. In Peeter; R. (ed.). Protides of the Biological Fluid Proceedings of the Collogium, 34; Brussels. Belgium Pergaman Press, Oxford, England. pp. 715-718.

Lerner, R. A. 1982. Nature 299:592-596.

Anon. 1989. Proc. of a Workshop on East Coast Fern Immunigation, T. T. Dolan (ed.) NAIROB, Kenya, pp. 187-188.

Creighton, T. E. 1983, *Protein:Structure and Molecular Principles*, W. H. Freeman and Company, New York, N.Y., pp. 93-98.

Pongor, S. 1987. Methods in Enzymology 154:450-473.

Bowie et al. 1990. Science 247:1306-1310.

*Primary Examiner*—Keith C. Furman
*Attorney, Agent, or Firm*—Townsend and Townsend

[57] ABSTRACT

This invention relates to the development of a vaccine against *Theileria parva*, which is a protozoan parasite infecting cattle in Africa. The invention specifically relates to the use of the 67 kDa glycoprotein from the surface of the *T. parva* sporozoite as an immunogen for inducing immunoprotection against *T. parva* in bovine species. This 67 kDa antigen is produced using recombinant genetics. Plasmids containing nucleic acid segments encoding the antigen, host cells containing the nucleic acid segments and recombinant methods for producing the antigen are part of this invention.

14 Claims, 10 Drawing Sheets

Figure 1A.

```
                                                              BclI
  1  TGA ACG ATG CAA ATA ACT CAG TTT TTG CTG ATC ATT CCG GTC TTA TTT GTA TCA GCA GGG..
  1          *** Met Gln Ile Thr Gln Phe Leu Leu Ile Ile Pro Val Leu Phe Val Ser Ala Gly

61  GAC AAA ATG CCT ACG GAG CAA GAA CAA TTT CCA TTT CCT TCT AGG CTT GGT CCC CTA GTA ACC TTG..
 19  Asp Lys Met Pro Thr Glu Gln Glu Gln Phe Pro Phe Pro Ser Arg Leu Gly Pro Leu Val Thr Leu

121  GAA TCA GCC ATA ACA CAA CCT ACC GCC GTG TAC ACA ATG AGG ACA GTT GGT AAT GTG GCA..
 39  Glu Ser Ala Ile Thr Gln Pro Thr Ala Val Tyr Thr Met Arg Thr Val Gly Asn Val Ala

181  AAG GCA GCA AAG GCA TGG AAG TCA GTA TCA TCT TCA GAT GTC TCT ACC ACT ATT CCC..
 59  Lys Ala Ala Lys Ala Trp Lys Ser Val Ser Ser Ser Asp Val Ser Thr Thr Ile Pro

241  ACT CCA GTT TCG GAA GAA AAT ATC CTT CAA ACA CAA ACG GAA GAA GTT CCT..
 79  Thr Pro Val Ser Glu Glu Asn Ile Leu Gln Thr Gln Thr Glu Glu Val Pro

301  GCT GCA AGC GGC TCA GAT TCA TAC ACT GTA ACA AAT TTG GTA CAA CAA TCC CAA GTT..
 99  Ala Ala Ser Gly Ser Asp Ser Tyr Thr Val Thr Asn Leu Val Gln Gln Ser Gln Val

361  CAG GAT AAT GTA AAG CAA CAG CAA GAT ACT AAG GGG AAC AGA TCA GAT TCC GAA GAA..
119  Gln Asp Asn Val Lys Gln Gln Gln Asp Thr Lys Gly Asn Arg Ser Asp Ser Glu Glu

421  AAT GAA GAT AGC ACC CTT AGT ACA GAT GTC TCT CCG ACC ATT CCT CCA GTT TCG GAA..
139  Asn Glu Asp Ser Thr Leu Ser Thr Asp Val Ser Pro Thr Ile Pro Pro Val Ser Glu
```

Figure 1B.

```
                                                                    PstI
481 GAA ATT ATC ACA CCT ACT CTT CAA GCA CAA ACG AAA GAA GTT CCT CCT GCA GAC CTC
159 Glu Ile Ile Thr Pro Thr Leu Gln Ala Gln Thr Lys Glu Val Pro Pro Ala Asp Leu

541 TCA GAT CAA GTT CCG TCA AAC GGC TCA GAC TCC GAA GAT AAT AAA TCC ACC TCA
179 Ser Asp Gln Val Pro Ser Asn Gly Ser Asp Ser Glu Asp Asn Lys Ser Thr Ser

601 TCT AAA GAT GAA AAG CTC AAA GAA CTC ACT CTA AAA ACA CCC GGA AAA TCC ACA GGT GAA
199 Ser Lys Asp Glu Lys Leu Lys Glu Leu Thr Leu Lys Thr Pro Gly Lys Ser Thr Gly Glu

661 ACT ACA TCG GGC CAA GAT CTC AAA AAT TCA AAA CAA CAG CAG GTT TCA GAT CTA GCC
219 Thr Thr Ser Gly Gln Asp Leu Lys Asn Ser Lys Gln Gln Gln Val Ser Asp Leu Ala

721 AGT GGA TCA CAC TCT GGA CTT AAA GTA CCT GGA GTT CCA GGT GCA GTT TCT
239 Ser Gly Ser His Ser Gly Leu Lys Val Pro Gly Val Pro Gly Ala Val Ser

781 CCC CAA GGT CAA TCT TTA GCT TCG AAT ACA TCT AGA GAA GGT CAG GCG CAG CAT CAA
259 Pro Gln Gly Gln Ser Leu Ala Ser Asn Thr Ser Arg Glu Gly Gln Ala Gln His Gln

841 CAG GTA GAT GGA GAT GGT AGA GTT ATT GAG CCT AAA ATT GGA TTA CCC GGA CCT CCA
279 Gln Val Asp Gly Asp Gly Arg Val Ile Glu Pro Lys Ile Gly Leu Pro Gly Pro Pro

901 TCT GCG CCA TCA CCA GGA GCG CCC GGA ATA ATT GTT AGA GAA TCA GGC AAT AGG
299 Ser Ala Pro Ser Pro Gly Ala Pro Gly Ile Ile Val Arg Glu Ser Gly Asn Arg
```

Figure 1C.

```
 961 GCA ATG GAT ATT GTA CAG TTT TTA GGA AGA TTT AAA CCA GAA CCA AGG GCA TAT GAA GGG
 319 Ala Met Asp Ile Val Gln Phe Leu Gly Arg Phe Lys Pro Glu Pro Arg Ala Tyr Glu Gly

1021 GAA AGA ACA AAT GTA GCA GAA CTA CTA AAA AAA TTC CTA TTT GAA GAA CTT GAA TCT TTG GTA
1339 Glu Arg Thr Asn Val Ala Glu Leu Leu Lys Lys Phe Leu Phe Glu Glu Leu Glu Ser Leu Val

1081 AAC ACT CTA ATA GAA TTG AAA TTA GCA ATT GCA AGC GAC TTT GTT GAA ATC ACT GAT GGT
1359 Asn Thr Leu Ile Glu Leu Lys Leu Ala Ile Ala Ser Asp Phe Val Glu Ile Thr Asp Gly
                                                       Tryptic peptide T18          EcoRI 1141 TTG AGA AAG AAT ACT AAA GAT CAT GAA GCC AGA TTG AAG CTA AGA GGT GTA GAA TTC
1379 Leu Arg Lys Asn Thr Lys Asp His Glu Ala Arg Leu Lys Leu Arg Gly Val Glu Phe 1201 ACT AAG AGG AAA AGT GTC GCC AAC GTA AAG GGA TTC AGT TCT TTG TAC TGT GTG CTT
1399 Thr Lys Arg Lys Ser Val Ala Asn Val Lys Gly Phe Ser Ser Leu Tyr Cys Val Leu 1261 TTA ATG AAT ATG AAC ATC AAA GAA AAA ACG AAA GAA TCT GAA GTA GCA GAT GGC ATT
1419 Leu Met Asn Met Asn Ile Lys Glu Lys Thr Lys Glu Ser Glu Val Ala Asp Gly Ile 1321 TGG AAA CTG TCT ACA ATC CCA GAT AAA GTA GCA AAT GAA CTT TTG TTA GCT ATG GAA AAG
1439 Trp Lys Leu Ser Thr Ile Pro Asp Lys Val Ala Asn Glu Leu Leu Leu Ala Met Glu Lys 1381 ATC GTG GTC CCA CCA AAA ACC CCT GAA CTA GAA GCG TTT GAG GCA ATC GAG TTT GGT
1459 Ile Val Val Pro Pro Lys Thr Pro Glu Leu Glu Glu Ala Phe Glu Ala Ile Glu Phe Gly
```

Figure 1D.

```
1441 TTC AAA ATA GCA TAC TAC GCA ACC AAA GAC ATC CTC TCA AGT ATA GAA AAC ACA GTT CAC
 479 Phe Lys Ile Ala Tyr Tyr Ala Thr Lys Asp Ile Leu Ser Ser Ile Glu Asn Thr Val His

1501 AAC TTG ATG CAC GCC AAA AAT TAT GAA GAG AAT TTT ATT GCT CAA GTA AGA AAC TCT CTA
 499 Asn Leu Met His Ala Lys Asn Tyr Glu Glu Asn Phe Ile Ala Gln Val Arg Asn Ser Leu
              KpnI

1561 AGG ATG GTA CCA CAC CAG ATG AAC ACT GAA TCG TTT GTA ATT AAA ATC TCA GAC
 519 Arg Met Val Pro His Gln Met Asn Thr Glu Ser Phe Val Ile Lys Ile Ser Asp

1621 ATG CGC AGA AGA ACA GCT AGT CAG GAC GAA CCA GCA GGA GCT GGG TCC GGA GTA
 539 Met Met Arg Arg Thr Ala Ser Gln Asp Glu Pro Ala Gly Ala Gly Ser Gly Val

1681 ACA CCA GGA CGA GGA TCA GGT ACG GGA CGA GCA GCA ACG GGA GGG GGA TCA CTG
 559 Thr Pro Gly Arg Gly Ser Gly Thr Gly Arg Ala Ala Thr Gly Gly Gly Ser Leu

1741 AGG GGA TTA GAC TTA AGT GAC GAA GAA GTT AAG AAA ATC TTG GAT GAA ATA GTG AAA GAT
 579 Arg Gly Leu Asp Leu Ser Asp Glu Glu Val Lys Lys Ile Leu Asp Glu Ile Val Lys Asp

1801 CCC AGC GAC GGA GAA CTT GGA CTC GGA CTT GTA AGT GAC CCA AGT GGA AGA TCA TCC GAA
 599 Pro Ser Asp Gly Glu Leu Gly Leu Gly Leu Val Ser Asp Pro Ser Gly Arg Ser Ser Glu
              Tryptic peptide T12

1861 AGA CAA CCC TCA CTC GGA CCT TCA CTT GTA ATA ACT GAT GGA CAA GCA GGA CCC ACA ATA
 619 Arg Gln Pro Ser Leu Gly Pro Ser Leu Val Ile Thr Asp Gly Gln Ala Gly Pro Thr Ile
```

Figure 1E.

```
1921 GTA TCT CCA ACA GGG CCC ACA ATA GCA GCT GGA GGA GAA CAA CCA CCT TCA GCT CCT AAT
 639 Val Ser Pro Thr Gly Pro Thr Ile Ala Ala Gly Gly Glu Gln Pro Pro Ser Ala Pro Asn

1981 GGA ACC GCA ACG GGG CCA GGA ACA CAA CCT GAG GGA GGA GGG GAG GAG AAG AAA GAA TTG
 659 Gly Thr Ala Thr Gly Pro Gly Thr Gln Pro Glu Gly Gly Gly Glu Glu Lys Lys Glu Leu

2041 ATA CAG AAG CTC AAG AAA CTC TGG GGG TCT GGA TTC GAA GTC GCG AGT CTT ATG ATA
 679 Ile Gln Lys Leu Lys Lys Leu Leu Gly Ser Gly Phe Glu Val Ala Ser Leu Met Ile

2101 CCA ATG GCG ACA ATA ATT ATC AGC ATC GTC CAC TAA CAA TAA CTC ACC TAA CCA CCC ACT
 699 Pro Met Ala Thr Ile Ile Ser Ile Val His ***     ***     ***     ***

2161 TAT TTA TAA CAC ACA CAA AAA AA
     ***             polyA tail
```

VACCINES FOR THE PROTECTION OF ANIMALS AGAINST THEILERIA INFECTION

This is a continuation of application Ser. No. 07/365,999 filed Jun. 14, 1989, now abandoned.

BACKGROUND OF THE INVENTION

1. Field of the Invention

This invention relates to the development of a vaccine against *Theileria parva*, which is a protozoan parasite infecting cattle in Africa. The invention specifically relates to the use of the 67 kDa glycoprotein from the surface of the *T. parva* sporozoite as an immunogen for inducing immunoprotection against *T. parva* in bovine species. This 67 kDa antigen is produced using recombinant genetics. Plasmids containing nucleic acid segments encoding the antigen, host cells containing the nucleic acid segments and recombinant methods for producing the antigen are part of this invention.

This invention also relates to the development of live vaccines against *Theileria parva*, which is a protozoan parasite infecting cattle in Africa. The invention specifically relates to the use of live attenuated strains of *Salmonella typhimurium* and vaccinia virus carrying the gene encoding the 67 kDa glycoprotein from the surface of the *T. parva* sporozoite as an immunogen for inducing immunoprotection against *T. parva* in bovine species. Construction of attenuated *S. typhimurium*, vaccinia viruses and plasmids containing nucleic acid segments encoding the antigen are a part of this invention. Finally this invention provides methods for immunoprotecting animals against *T. parva* infection.

The protozoan parasite, *Theileria parva,* which is transmitted by the ixodid tick, *Rhipicephalus appendiculatus,* causes East Coast fever (ECF), a disease of cattle which continues to exert severe limitations on the development of the livestock industry in much of Eastern and Central Africa. *T. parva* is divided into three sub-types, *T. parva parva, T. parva bovis* and *T. parva lawrencei.* This classification is based on certain epidemiological and behavioral characteristics of the parasites. *T. parva* lawrencei originates from buffalo and is highly pathogenic to cattle. *T. parva bovis* and *T. parva* parva are maintained between cattle and differ in pathogenicity. Despite this classification there is no definitive proof for sub-speciation of *T. parva.* For the purposes of this document, *T. parva* therefore encompasses all three sub-types which are themselves heterogenous in nature.

Infection with *T. parva* is initiated when sporozoites are inoculated into the mammalian hosts by the tick during feeding. The sporozoites enter lymphocytes where they mature into schizonts. The intralymphocytic schizonts later develop to merozoites which enter erythrocytes to become piroplasms which are ingested by ticks feeding on the parasitized host. Gametes which develop from the piroplasms fuse to initiate the parasite life cycle in the tick which culminates in the production of sporozoites in the tick salivary gland.

Information Disclosure

Theileria infections of cattle have been recognized as a cause of a serious and often lethal disease of cattle since the early 1900's. A review of the disease can be found in Irvin A. D. and Morrison W. I. Immune Responses in Parasitic Infection: Immunology, immunopathology, and immunoprophylaxis Vol. III, Ed. E. J. L. Soulsby CRC Press Inc. Florida, 1987, pp 223-274. *T. parva* infection results in a high rate of mortality; however, some animals recover from the infection and are subsequently immune to homologous challenge. At present, it is possible to induce immunity by infecting cattle with sporozoites and simultaneously administering oxytetracycline. Radley, D. E., et al., 1975, East Coast fever: 1. Chemoprophylactic immunization of cattle against *Theileria parva* (Muguga) and five theilerial strains. Vet Parasitol. 1:35–41; and Radley et al., 1975, East Coast fever: 3. Chemoprophylactic immunization of cattle using oxytetracycline and a combination of theilerial strains Vet. Parasitol. 1, 51-60. However, this method of immunization affords protection against only a limited number of different *T. parva* isolates, Radley, D. E. et al., 1975. East Coast fever. 2. Cross-immunity trials with a Kenya strain of Theileria lawrencei. Vet. Parasitol. 1: 43–50; Cunningham, M. P., et al., 1974, Theileriosis: The exposure of immunized cattle in a Theileria lawrencei enzootic area. Trop. Anim. Hlth. 6, 39–43; and Irvin, A. D., et al., 1983, Immunization against East Coast fever: correlation between monoclonal antibody profiles of *Theileria parva* isolates and cross immunity in vivo. Res. Vet. Sci. 35:341-346].

It has been shown that animals which have developed immunity to *T. parva* exhibit antibody responses against proteins of the sporozoite stage (Musoke, A. J., et al., 1982, Bovine immune response to *Theileria parva:* neutralizing antibodies to sporozoites, Immunology 45:663–668) as well as a cell-mediated response against the schizont stage (Eugui, E. M. and Emery, D. L., 1981, Genetically restricted cell-mediated cytotoxicity in cattle immune to *Theileria parva.* Nature 290, 251–254). There is evidence that antibodies raised against sporozoite antigens can block infectivity in vitro in a non-isolate specific manner (Musoke, A. J., et al., 1984, Evidence for a common protective antigenic determinant on sporozoites of several *Theileria parva* strains. Immunology 52, 231–238; and Dobbelaere, D. A. E., 1984, Monoclonal antibody neutralizes the sporozoite stage of different *Theileria parva* isolates, Parasite Immunol. 6:361–370). However, the extent of protection conferred in cattle by this humoral response, and the role played by particular sporozoite antigens, have not yet been reliably evaluated.

The 67 kDa antigen that is the subject of this invention was previously known to be an antigen on the sporozoite surface (Dobbelaere, D. A. E. et al., 1985, Identification of a surface antigen on *Theileria parva* sporozoites by monoclonal antibody, Proc. Natl. Acad. Sci., U.S.A. 82:1771–1775; and Dobbelaere, D. A. E. et al., 1985, *Theileria parva:* Expression of a sporozoite surface coat antigen, Experimental Parasitology, 60:90–25).

DESCRIPTION OF FIGURES

FIG. 1. DNA and inferred amino acid sequence of the sporozoite 67 kDa gene.

The DNA sequence corresponding to the open reading frame up to the polyA tail is shown. The position of important restriction enzyme sites is marked. The site of cleavage of the signal sequence to release the mature sporozoite antigen was predicted according to Perlman and Halvorson, 1983, J.Mol.Biol. 167:391–409. As judged by these "rules" the cleavage site could be at any one of three positions; between residues 16–17, 17–18 and 18–19.

FIG. 2. The recombinant vector phTpp(mug)-p67 sp comprising the sporozoite 67 kDa antigen that has been deposited.

FIG. 3. Construction of an expression plasmid for production of the 67 kDa antigen in *E. coli* involving the use of a full length cDNA.

FIG. 4. Assembly of a prokaryotic expression plasmid from Theileria cDNA and genomic DNA.

FIG. 5. Construction of an expression plasmid for production of the 67 kDa antigen in mouse cells using full length cDNA.

FIG. 6. Construction of an expression plasmid for production of the 67 kDa antigen in mouse cells using sequences assembled from cDNA and genomic DNA.

SUMMARY OF THE INVENTION

This invention provides for a composition of substantially pure *Theileria parva* sporozoite surface glycoprotein of about 67 kDa or modifications thereof having immunological crossreactivity with *Theileria sera* said glycoprotein having the amino acid sequence set forth in FIG. 1. When this glycoprotein is produced by bacteria which have been genetically altered to express the glycoprotein the composition will be devoid of carbohydrate side chains ordinarily attached by eukaryote cells. It is preferred that the compositions of this invention are substantially free of other proteins or polypeptides of Theileria origin. By Theileria origin, we refer to proteins derived from or originating from species of this genus of protozoa.

This invention also provides for recombinant DNA sequences comprising a DNA segment encoding a *Theileria parva* sporozoite surface glycoprotein of about 67 kDa or modifications thereof having immunological crossreactivity with *Theileria sera*, said glycoprotein having the amino acid sequence set forth in FIG. 1. It is also disclosed herein, that the above segment may be recombined in positions adjacent to either DNA sequences derived from vaccinia virus or adjacent to DNA sequences derived from Salmonella type bacteria. The preferred salmonella type bacteria are *Salmonella typhimurium*.

The DNA segment described above may also be made a part of a recombinant DNA plasmid. Such plasmids would preferably direct the expression of the glycoprotein in a bacterial or eukaryote host cell. The preferred host cells are selected from the group consisting of *Escherichia coli* and *Salmonella typhimurium*.

This invention also provides for vaccines for inducing immunoprotection in animals against infections with species of Theileria comprising at least one active ingredient selected from the group consisting of a substantial pure sporozoite surface glycoprotein of about 67 kDa; a modification of a said glycoprotein having immunological crossreactivity with *Theileria sera;* a sequence of DNA encoding said glycoprotein; and a sequence of DNA encoding said modification of said glycoprotein; wherein the glycoprotein has the amino acid sequence set forth in FIG. 1. These vaccines may also include compositions comprising live Salmonella bacteria capable of expressing the *Theileria parva* sporozoite surface glycoprotein as described above. These salmonella bacteria may carry the glycoprotein gene either as a stably maintained expression plasmid or as a segment of DNA integrated into its chromosome.

Alternatively, the vaccine may comprise vaccinia virus modified to express in infected cells the *Theileria parva* sporozoite surface glycoprotein of about 67 kDa or a modification thereof as defined above.

The vaccines of this invention are preferably protective against infection from *Theileria parva*.

There is also disclosed herein a method for protecting animals from infections of species of Theileria comprising the administration of an effective amount of a vaccine comprising at least one active ingredient selected from the group consisting of a substantially pure sporozoite surface glycoprotein of about 67 kd; a modification of a said glycoprotein having immunological crossreactivity with *Theileria sera;* a sequence of DNA encoding said glycoprotein; or a sequence of DNA encoding said modification of said glycoprotein; wherein the glycoprotein has the amino acid sequence set forth in FIG. 1. Said method can be conducted with any of the vaccines described above or combinations thereof.

A culture deposit of *E.coli* containing recombinant plasmids encoding the Theileria 67 kDa antigen has been made. The culture was deposited with the National Collections of Industrial Bacteria Limited (NCIMB) at 15 Abbey Road, Aberdeen AB9 8DG, Scotland, U.K., on May 15, 1989 and given an Accession Number of NCIMB 40147. See FIG. 2 for a restriction enzyme map of the deposited plasmid, phTpp(mug)-p67sp.

DETAILED DESCRIPTION

Figure 2:
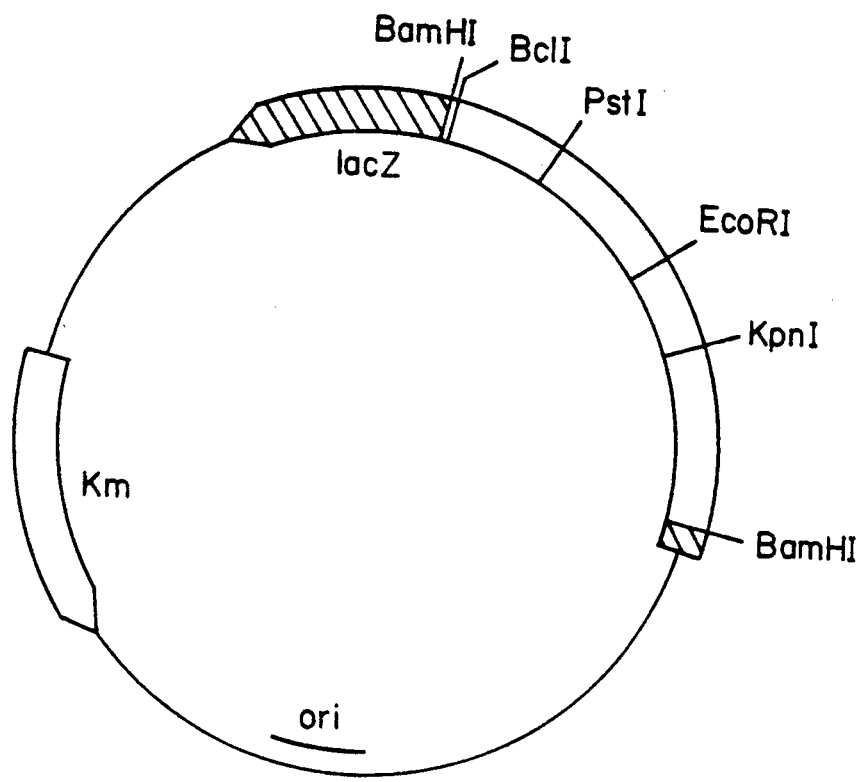

This invention provides for means of producing the 67 kDa antigen in quantities that will permit large scale vaccination of cattle against *T. parva*. The current immunization procedure of administering the infective parasite followed by drug treatment is not practical. The procedure requires a good veterinary infrastructure which is not generally available. An expensive liquid nitrogen facility is required for storage of the parasite. Furthermore, the parasites may also become an accidental source of infection to the animals.

A purified 67 kDa antigen is more practical and effective as an active component in a vaccine. At least one antigenic determinant on the 67 kDa antigen of *T. parva* parva (Muguga) is conserved since one monoclonal antibody will in an in vitro assay neutralise sporozoites from different isolates of the parasites. The 67 kDa antigen should therefore afford protection against all sub-types of *T. parva*.

The large scale isolation of sporozoites as a source of the 67 kDa antigen is not a practical means of producing a vaccine as the sporozoites must be isolated from the dissected salivary glands of ticks. In addition tick infection rates vary considerably making it difficult to consistently obtain large numbers of sporozoites.

Rather than extract the 67 kDa antigen directly from sporozoites, one can use recombinant genetics to facilitate the production of the Theileria antigen. One standard method would involve the introduction of DNA encoding the 67 kDa sporozoite surface antigen into a suitable host cell, followed by induction of that cell to produce large amounts of the selected protein. This invention embraces such molecular genetic manipulations. The following descriptions will detail the various methods available to express genes encoding Theileria antigens, and is followed by specific examples of preferred methods.

An alternative method involves the administration of live *S. typhimurium* or vaccinia virus that contains the gene encoding the 67 kDa antigen. Live vaccines will induce a potent immune response against *T. parva*, without the need for purification of the 67 kDa antigen. The following descriptions also detail various methods available to express genes encoding Theileria antigens in *Salmonella typhimurium* and vaccinia, and is followed by specific examples of preferred methods.

A. General Methods

Much of the nomenclature and general laboratory procedures required in this application can be found in Maniatis, T. et al., Molecular Cloning—A Laboratory Manual, Cold Spring Harbor Laboratory, Cold Spring Harbor, N.Y., 1982. The manual is hereinafter referred to as "Maniatis".

All *E. coli* and *S. typhimurium* strains are grown in Luria broth (LB) or M9 medium supplemented with glucose and acid-hydrolyzed casein amino acids. Strains with resistance to antibiotics are maintained at the drug concentrations described in Maniatis.

Vaccinia virus is grown in suitable cultured mammalian cells such as the HeLA S3 spinner cells, as described by Mackett, Smith and Moss, "The construction and characterization of Vaccinia Virus Recombinants Expressing Foreign Genes" in "DNA cloning Vol. II. A practical approach", Ed. D. M. Glover, IRL Press, Oxford, pp 191-211.

All enzymes are used according to the manufacturer's instructions.

cDNA libraries were constructed in bacteriophage lambda gt11. Phage are packaged in vitro, and recombinant phage were analyzed by plaque hybridization as described in Benton and Davis, Science 196: 180-182 1977 and in Maniatis. Lambda gt11 DNA and the in vitro packaging system can be obtained from Promega Biotec.

DNA was sequenced using the dideoxy procedure of Sanger. F. et al., 1977, PNAS 74: 5463-5467 or by the modified T7 DNA polymerase procedure of Tabor and Richardson, 1987, PNAS, 84: 4767-4771. The latter was obtained as a kit (Sequanase) from U.S. Biochemicals and used according to the manufacturer's instruction.

Polynucleotide sizes are given in either kilo-base pairs (kb) or basepairs (bp). These are either estimates derived from agarose gel electrophoresis or actual sizes determined by DNA sequencing. B. Theileria 67 kDa Sporozoite Surface Antigen cDNA The first step in obtaining expression of the gene encoding the 67 kDa antigen is to obtain the DNA sequence coding for the protein from cDNA clones. A full length cDNA is then cloned into an expression vector which is capable of directing efficient transcription and translation of the gene.

The method for obtaining cDNA has been described generally in Maniatis. Parasite messenger RNA is converted into cDNA as described by Gubler and Hoffman, 1983, Gene, 25: 263-269. A library of clones is prepared by adding EcoRI linkers to the cDNA, ligating the cDNA to EcoRI digested DNA arms of lambda gt11 and packaging the ligated DNA into viable phage particles. The clones containing antigen cDNA are detected by hybridization with probes of labelled synthetic oligonucleotides complementary to portions of the cDNA sequence (Wallace, R. B., et al., 1981, Nucleic Acids Res. 9: 879-894), followed by restriction enzyme analysis and DNA sequencing.

The synthetic oligonucleotide probes are single-stranded DNA molecules, typically between 10 and 50 nucleotides in length. FIG. 1 provides the nucleic acid sequence of the 67 kDa antigen from which suitable oligonucleotide probes may be derived.

Oligonucleotides for use as probes are chemically synthesized according to the solid phase phosphoramidite triester method first described by Beaucage, S. L. and Caruthers, M. H., 1981, Tetrahedron Letts., 22(20):1859-1862 using an automated synthesizer, as described in Needham-VanDevanter, D. R., et al., 1984, Nucleic Acids Res., 12:6159-6168. Purification of oligonucleotides is by either native acrylamide gel electrophoresis or by anion-exchange HPLC as described in Pearson, J. D. and Regnier, F. E., 1983, J. Chrom., 255:137-149.

The sequence of the synthetic oligonucleotides can be verified using the chemical degradation method of Maxam, A. M. and Gilbert, 1980, in W., Grossman, L. and Moldave, D., eds. Academic Press, New York, Methods in Enzymology, 65:499-560.

C. Expression in Prokaryotes

To obtain high level expression of a cloned gene, such as those cDNAs encoding Theileria antigens in a prokaryotic system, it is essential to construct expression plasmids which contain, at the minimum, a strong promoter to direct transcription, a ribosome binding site for translational initiation, and a transcription/translation terminator. Examples of regulatory regions suitable for this purpose in *E. coli* are the promoter and operator region of the *E. coli* tryptophan biosynthetic pathway as described by Yanofsky, C., 1984, J. Bacteriol., 158:1018-1024 and the leftward promoter of phage lambda ($P_L$) as described by Herskowitz, I. and Hagen, D., 1980, Ann. Rev. Genet., 14:399-445.

Expression systems for expressing the 67 kDa antigens are available using *E. coli,* Bacillus sp. (Palva, I et al., 1983, Gene 22:229-235; Mosbach, K. et al., Nature, 302:543-545 and Salmonella. *E. coli* and Salmonella systems are preferred.

The 67 kDa antigen produced by prokaryote cells will not be glycosylated and the antigen may not necessarily fold properly. During purification from *E. coli,* the expressed antigen protein may first be denatured and then renatured. This can be accomplished by solubilizing the bacterially produced proteins in a chaotropic agent such as guanidine HCl and reducing all the cysteine residues with a reducing agent such as beta- mercaptoethanol. The protein is then renatured, either by slow dialysis or by gel filtration. U.S. Pat. No. 4,511,503.

Detection of the expressed antigen is achieved by methods known in the art as radioimmunoassays, or Western blotting techniques or immunoprecipitation. Purification from *E. coli* can be achieved following procedures described in U.S. Pat. No. 4,511,503.

D. Expression in *S. typhimurium*

A serious limitation to the expression of heterologous gene products from plasmids in Salmonella is that the commonly used plasmid cloning vectors are inherently unstable. To circumvent this, the foreign gene can be incorporated into a nonessential region of the host chromosome. This is achieved by first inserting the gene into a plasmid such that it is flanked by regions of DNA homologous to the insertion site in the Salmonella chromosome. After introduction of the plasmid into the *S. typhimurium,* the foreign gene is incorporated into the chromosome by homologous recombination between the flanking sequences and chromosomal DNA.

An example of how this could be achieved is based on the his operon of Salmonella. Two steps are involved in this process. Firstly, a segment of the his operon must be deleted in the Salmonella strain selected as the carrier. Secondly, a plasmid carrying the deleted his region downstream of the gene encoding the 67 kDa antigen is transformed into the his Salmonella strain. Integration of both the his sequences and the gene encoding the 67 kDa antigen occurs, resulting in recombinant strains which can be selected as His[30].

Detection of the expressed antigen is achieved by methods known in the art such as radioimmunoassays, Western blotting or immunoprecipitation.

The Salmonella strain used in the vaccine is derived from strains normally virulent for cattle. Specific attenuation of the strains render the bacteria avirulent but still capable of inducing a potent immune response after inoculation into cattle. An example of such a strain is the aro A mutant of *S. typhimurium* (Smith B. P. et al., Am. J. Vet. Res. 45:59–66).

E. Synthesis of the Theileria Antigen Proteins in Eukaryotes

The Theileria 67 kDa antigen is a glycoprotein. Prokaryotic expression systems generally lack the ability to glycosylate eukaryotic proteins. Therefore, it is often advantageous to express a particular protein in an eukaryotic system, especially when a significant proportion of the immunogenicity resides in the carbohydrate portion of the antigen.

1. Expression in recombinant vaccinia virus-infected cells

The gene encoding the 67 kDa antigen is inserted into a plasmid designed for producing recombinant vaccinia, such as pG562, Langford, C. L., et al., 1986, Mol. Cell. Biol. 6:3191–3199. This plasmid consists of a cloning site for insertion of foreign genes, the P7.5 promoter of vaccinia to direct synthesis of the inserted gene, and the vaccinia TK gene flanking both ends of the foreign gene.

When the plasmid containing the 67 kDa antigen gene is constructed, the gene can be transferred to vaccinia virus by homologous recombination in the infected cell. To achieve this, suitable recipient cells are transfected with the recombinant plasmid by standard calcium phosphate precipitation techniques into cells already infected with the desirable strain of vaccinia virus, such as Wyeth, Lister, WR or Copenhagen. Homologous recombination occurs between the TK gene in the virus and the flanking TK gene sequences in the plasmid. This results in a recombinant virus with the foreign gene inserted into the viral TK gene, thus rendering the TK gene inactive. Cells containing recombinant viruses are selected by adding medium containing 5-bromodeoxyuridine, which is lethal for cells expressing a TK gene.

Confirmation of production of recombinant virus can be achieved by DNA hybridization using cDNA encoding the 67 kDa antigen and by immunodetection techniques using antibodies specific for the expressed protein. Virus stocks may be prepared by infection of cells such as HeLA S3 spinner cells and harvesting of virus progeny.

2. Expression in Yeast

Synthesis of heterologous proteins in yeast is well known and described. Methods in Yeast Genetics, Sherman, F., et al., Cold Spring Harbor Laboratory, (1982) is a well recognized work describing the various methods available to produce the Theileria 67 kDa antigen in yeast.

For high level expression of a gene in yeast, it is essential to connect the gene to a strong promoter system as in the prokaryote and also to provide efficient transcription termination/polyadenylation sequences from a yeast gene. Examples of useful promoters include GAL1,10 (Johnson, M., and Davies, R. W., 1984, Mol. and Cell. Biol., 4:1440-1448) ADH2 (Russell, D., et al., 1983, J. Biol. Chem., 258:2674-2682), PHO5 (EMBO J. 6:675-680, 1982), and MFα1. A multicopy plasmid with a selective marker such as Leu-2, URA-3, Trp-1, and His-3 is also desirable.

The MFα1 promoter is preferred. The MFα1 promoter, in a host of the α mating-type is constitutive, but is switched off in diploids or cells with the a mating-type. It can, however, be regulated by raising or lowering the temperature in hosts which have a ts mutation at one of the SIR loci. The effect of such a mutation at 35° C. on an α type cell is to turn on the normally silent gene coding for the α mating-type. The expression of the silent a mating-type gene, in turn, turns off the MFα1 promoter. Lowering the temperature of growth to 27° C. reverses the whole process, i.e., turns the a mating-type off and turns the MFα1 on (Herskowitz, I. and Oshima, Y., 1982, in The Molecular Biology of the Yeast Saccharomyces, (eds. Strathern, J. N. Jones, E. W., and Broach, J. R., Cold Spring Harbor Lab., Cold Spring Harbor, N.Y., pp.181-209.

The polyadenylation sequences are provided by the 3'-end sequences of any of the highly expressed genes, like ADH1, MFα1, or TPI (Alber, T. and Kawasaki, G., 1982, J. of Mol. & Appl. Genet. 1:419-434.

A number of yeast expression plasmids like YEp6, YEp13, YEp4 can be used as vectors. A gene of interest can be fused to any of the promoters in various yeast vectors. The above-mentioned plasmids have been fully described in the literature (Botstein, et al., 1979, Gene, 8:17-24; Broach, et al., 1979, Gene, 8:121-133).

Two procedures are used in transforming yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in the papers by J. D. Beggs, 1978, Nature (London), 275:104-109; and Hinnen, A., et al., 1978, Proc. Natl. Acad. Sci. U.S.A., 75:1929-1933. The second procedure does not involve removal of the cell wall. Instead the cells are treated with lithium chloride or acetate and PEG and put on selective plates (Ito, H., et al., 1983, J. Bact., 153:163-168).

The Theileria 67 kDa sporozoite surface antigen can be isolated from yeast by lysing the cells and applying standard protein isolation techniques to the lysates. The monitoring of the purification process can be accomplished by using Western blot techniques or radioimmunoassays.

3 Expression in Cell Cultures

The Theileria 67 kDa antigen cDNA can be ligated to various expression vectors for use in transforming host cell cultures. The vectors typically contain gene sequences to initiate transcription and translation of the Theileria antigen gene. These sequences need to be compatible with the selected host cell. In addition, the vectors preferably contain a marker to provide a phenotypic trait for selection of transformed host cells such as dihydrofolate reductase or metallothionein. Additionally, a vector might contain a replicative origin.

Illustrative of cell cultures useful for the production of the Theileria antigen are cells of insect or mammalian origin. Mammalian cell systems often will be in the form of monolayers of cells although mammalian cell suspensions may also be used. Illustrative examples of mammalian cell lines include VERO and HeLa cells, Chinese hamster ovary (CHO) cell lines, W138, BHK, COS-7 or MDCK cell lines.

As indicated above, the vector, e.g., a plasmid, which is used to transform the host cell, preferably contains DNA sequences to initiate transcription and sequences to control the translation of the antigen gene sequence. These sequences are referred to as expression control sequences. When the host cell is of insect or mammalian origin illustrative expression control sequences are obtained from the SV-4O promoter (Science, 222:524-527, 1983), the CMV I. E. Promoter (Proc. Natl. Acad. Sci. 81:659-663, 1984) or the metallothionein promoter (Nature 296:39-42, 1982). The cloning vector containing the expression control sequences is cleaved using restriction enzymes and adjusted in size as necessary or desirable and ligated with cDNA coding for the Theileria 67 kDa antigen by means well known in the art.

As with yeast, when higher animal host cells are employed, polyadenlyation or transcription terminator sequences from known mammalian genes need to be incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, J. et al., 1983, J. Virol. 45: 773-781).

Additionally gene sequences to control replication in the host cell may be incorporated into the vector such as those found in bovine papilloma virus type-vectors. Saveria-Campo, M., 1985, "Bovine Papilloma virus DNA a Eukaryotic Cloning Vector" in DNA Cloning Vol.II a Practical Approach Ed. D. M. Glover, IRL Press, Arlington, Va. pp. 213-238.

The host cells are competent or rendered competent for transformation by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electropora-tion and micro-injection of the DNA directly into the cells.

The transformed cells are cultured by means well known in the art. Biochemical Methods in Cell Culture and Virology, Kuchler, R. J., Dowden, Hutchinson and Ross, Inc., (1977). The expressed theilerial antigen is isolated from cells grown as suspensions or as monolayers. The latter are recovered by well known mechanical, chemical or enzymatic means.

Isolation of the Theileria antigen can be accomplished by lysing the host cells with detergents. Further purification is accomplished by affinity, ion-exchange or gel filtration chromatography using the procedures generally used to purify the antigen from sporozoites. (See generally, Pharmacia Fine Chemicals literature: Affinity Chromatography Principles and Methods, Ion Exchange Chromatography Principle and Methods and Gel Filtration Theory and Practice.)

F. Vaccines Against *Theileria parva* a) General, non-vectored

A vaccine prepared utilizing the Theileria 67 kDa antigen or immunogenic equivalents thereof can comprise: (a) a crude cell extract of *T.parva* sporozoites or a suspension of chemically fixed sporozoites; (b) a crude extract of cells recombinantly altered to express the Theileria 67 kDa antigen or a chemically-fixed suspension of such cells; (c) a partially or completely purified Theileria antigen preparation. The antigen produced by recombinant DNA technology is preferred because it is more economical than the other sources and is more readily purified in large quantities. The 67 kDa antigen can be prepared in unit dose form by well-known procedures. The vaccine can be administered intramuscularly or subcutaneously. For parenteral administration, such as by subcutaneous injection, the antigen may be combined with a suitable carrier. For example, it may be administered in water, saline or buffered vehicles with or without various adjuvants or immunomodulating agents such as aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid, *Propionobacterium acnes*, (*Corynebacterium parvum*), *Bordetella pertussis*, polyribonucleotides, sodium alginate, lanolin, lysolecithin, vitamin A, saponin, liposomes, levamisole, DEAE-dextran, Iscoms (Morein et al., (1984), Nature 408: 457-460), blocked copolymers or other synthetic adjuvants. Such adjuvants are available commercially from various sources, for example, Merck Adjuvant 6 (Merck and Company, Inc., Rahway, N.J.). Other suitable adjuvants are Freund's Incomplete Adjuvant (Difco Laboratories, Detroit, Mich.) and MPL+TDM Emulsion (RIBBI Immunochem Research Inc. U.S.A.). Other immunostimulants include interleukin 1, interleukin 2 and interferon-gamma. These proteins can be provided with the vaccine or their corresponding genetic sequence provided as a functional operon with a recombinant vaccine system such as vaccinia virus. The proportion of antigen and adjuvant can be varied over a broad range so long as both are present in effective amounts. For example, aluminum hydroxide can be present in an amount of about 0.5% of the vaccine mixture ($Al_2O_3$ basis). On a per-dose basis, the concentration of the antigen can range from about 1.0 ug to about 100 mg per bovine host. A preferable range is from about 100 ug to about 3.0 mg per unit dose. A suitable dose size is about 1-10 ml, preferably about 1.0 ml. Accordingly, a dose for subcutaneous injection, for example, would comprise 1 ml containing 1.0 mg of antigen and 3 mg of saponin.

For the initial vaccination of immunologically naive cows, a regimen of between 1 and 4 unit doses can be used with the injections spaced out over a 2- to 6-week period. Typically, a two-dose regimen is used. The second dose of the vaccine then should be administered some weeks after the first dose, for example, about 4 to 8 weeks later. Animals that have been previously exposed to *Theileria parva* or have received colostral antibodies from the mother may require booster injections. The booster injection is preferably timed to coincide with times of maximal challenge. Different immunization regimes may be adopted depending on the prevailing climate of the region. Semi-annual revaccination is recommended for breeding animals. Steers and bulls may be revaccinated at any time. Also, cows can be revaccinated before breeding. Calves may be vaccinated at about 2 to 3 months after birth, again at 4 to 6 months, and yearly or preferably semi-annually thereafter.

The vaccine may also be combined with vaccines for other diseases to produce multivalent vaccines. It may also be combined with other medicaments, for example, antibiotics. A pharmaceutically effective amount of the vaccine can be employed with a pharmaceutically acceptable carrier or diluent understood to be useful for the vaccination of animals such as swine, cattle, sheep, goats, and other mammals. These additives including adjuvants are referred to as "injectables of non-Theileria parva origins." Other vaccines may be prepared according to methods well-known to those skilled in the art as set forth, for example, in I. Tizard, An Introduction to Veterinary Immunology, 2nd Ed, 1982, which is incorporated herein by reference.

b) *S. typhimurium*

A vaccine prepared utilizing the gene encoding the 67 kDa antigen expressed in *S. typhimurium* can comprise either a) live attenuated *S. typhimurium* harboring a stable plasmid containing the gene encoding the 67 kDa antigen in a form suitable for expression of the gene or b) live attenuated *S. typhimurium* in which the gene encoding the 67 kDa antigen has been incorporated into the host chromosome in a form suitable for expression of the gene.

For the initial vaccination of immunologically naive cows, a typical regimen would consist of two doses of $10^9$ bacteria/dose delivered 1 week apart. The intramuscular route is preferred as this would minimize release of the bacterium into the environment.

c) Vaccinia virus

A vaccine prepared utilizing the gene encoding the 67 kDa antigen incorporated into vaccinia virus would comprise stocks of recombinant virus where the gene encoding the 67 kDa antigen is integrated into the genome of the virus in a form suitable for expression of the gene.

For the initial vaccination of immunologically naive cows, a typical regimen would consist of two doses of $4 \times 10^8$ plaque forming units (p.f.u.) of virus, inoculated intra-muscularly four weeks apart.

G. Definitions

The phrase "cell culture" refers to the containment of growing cells derived from a multi-cellular plant or animal which allows for the cells to remain viable outside the original plant or animal.

The term "microorganism" includes both single cellular prokaryote and eukaryote organisms such as bacteria, actinomycetes and yeast.

The term "plasmid" refers to an autonomous self-replicating circular DNA molecule and includes both the expression and nonexpression types. Where a recombinant microorganism or cell culture is described as hosting an "expression plasmid", this includes both extrachromosomal circular DNA molecules and DNA that has been incorporated into the host chromosome(s). Where a plasmid is being maintained by a host cell, the plasmid is either being stably replicated by the cells during mitosis as an autonomous structure or is incorporated within the host's genome.

The phrase "substantially pure," in the context of the Theileria 67 kDa antigen, refers to compositions containing the Theileria 67 kDa sporozoite surface antigen or protein derivative. Substantially pure antigen may be contaminated with low levels of protein from the *Theileria parva* sporozoites, or from recombinant host cell constituents. The amount of contaminating proteins is such that the vaccinated animal will not respond with significant levels of antibodies against said contaminants. Typically, the antigen preparation will be pure to at least 75%, preferably at a purity in excess of 95%, and most preferably in excess of 98%.

The phrase "Theileria 67 kDa sporozoite surface antigen" unless otherwise stated, is meant to include both the naturally occurring sporozoite surface glycoprotein, and protein derivatives embracing deletions and changes in the amino acid sequence and carbohydrate side chains such that they appear to the immune system as functional equivalents for purposes of protection from Theileria infection. These non-natural derivatives are also known as "immunogenic equivalents". Those of skill will readily recognize that it is only necessary to expose a mammal to appropriate epitopes in order to elicit effective immunoprotection. The epitopes are typically segments of amino acids which are a small portion of the whole protein. Using recombinant genetics it is simple and routine to alter a natural protein's primary structure to create derivatives embracing epitopes that are identical to or substantially the same as (immunologically equivalent to) the naturally occurring epitopes. Such proteins would exhibit cross reactivity with the antisera produced against the natural 67 kDa antigen. These protein derivatives may include peptide fragments, amino acid substitutions, amino acid deletions and amino acid additions within the natural amino acid sequence for the Theileria 67 kDa antigens. For example, it is known in the protein art that certain amino acid residues can be substituted with amino acids of similar size and polarity without an undue effect upon the biological activity of the protein or its antigenicity. In the primary sequence of the theilerial antigen, the following residues are generally considered to be interchangeable in non-critical regions: (1) alanine, leucine, isoleucine, valine and proline are interchangeable, (2) phenylalanine and tryptophan are interchangeable, (3) serine, threonine and tyrosine are interchangeable, (4) asparagine and glutamine are interchangeable, (5) lysine, arginine, histidine and ornithine are interchangeable, and (6) aspartic acid and glutamic acid are interchangeable.

The phrase "DNA sequence" refers to a single or double stranded DNA molecule composed of nucleotide bases, adenosine, thymidine, cytosine and guanosine.

The phrase "suitable host" refers to a cell culture or microorganism that is compatible with a recombinant plasmid and will permit the plasmid to replicate, to be incorporated into its genome or to be expressed.

The phrase "*Theileria sera*" refers to blood serum containing antibodies reactive with native 67 kDa antigen.

EXAMPLE 1

Cloning of the 67 kDa glycoprotein gene from Theileria sporozoite mRNA

A. Parasite Stabilates

*T. parva* sporozoites are derived from stabilate Muguga 10. For piroplasm preparation, calves, 6 to 12 months of age, are infected by inoculation with a sporozoite stabilate prepared as previously described in Cunningham, M. P., et al., 1973, Int. J. Parasit. 3:583–587.

B. Construction of a cDNA library in lambda gt 11

The following procedure details the isolation of Theileria cDNA encoding the 67 kilodalton glycoprotein of the sporozoites using a synthetic DNA probe complementary to the 5' end of the gene which codes for the N-terminal amino acid sequence of the protein. The DNA sequence and inferred amino acid sequence of the Theileria antigen gene are provided in FIG. 1.

Dissected salivary glands from *T. parva parva* (Muguga) infected ticks fed for three days on rabbits are flash frozen in liquid nitrogen. Total RNA is isolated from the salivary glands using the hot phenol/SDS method as described by Cordingley, J. S. et al., 1983, Gene 26: 25-39. The glands are ground to a fine powder in liquid nitrogen using a pestle and mortar. The powder is added to five volumes of a 1:1 mixture of water saturated phenol and NETS [20 mM Tris pH 7.8, 200 mM NaCl, 2 mM EDTA, 1% SDS] at 85° C. and mixed until homogenous. The mixture is cooled, centrifuged and the upper aqueous phase is recovered. The phenol layer is re-extracted with a half volume of NETS at 85° C. and the pooled aqueous phases is re-extracted with aqueous phenol. Nucleic acids are precipitated out of solution by the addition of two volumes of ethanol and are collected by centrifugation. This preparation is enriched for single stranded nucleic acids by two rounds of LiCl precipitation. Three volumes of 4M LiCl are added to the dissolved RNA preparation and the mixture is incubated on ice for 1 hour. The precipitate is recovered. washed with 70% ethanol, dried and the whole procedure is repeated. Poly-A RNA is selected from this enriched RNA fraction by two rounds of purification on an oligo-dT cellulose column [Collaborative Research Inc., type 3] as described by the manufacturer. Messenger RNA is concentrated by ethanol precipitation and is re-dissolved in sterile distilled water.

Approximately 10 ug of poly-A RNA are converted into double stranded cDNA using the Bethesda Research Laboratories Inc. cDNA synthesis kit according to the manufacturer's instructions. The cDNA is methylated to protect internal EcoRI restriction sites. The synthetic linker CGGAATTCCG [New England Biolabs #1004] containing the EcoRI restriction site is phosphorylated with polynucleotide kinase and it is ligated to the cDNA with T4 DNA ligase. The ligated DNA is digested with EcoRI to create cohesive ends and the cDNA is size fractionated on a Sephacryl S-500 column [Pharmacia]. The cDNA was ligated to dephosphorylated lambda gt11 arms [Promega Biotec] and packed into phage particles in vitro using the Packagene system [Promega Biotec] according to the manufacturer's instructions. These phage particles constitute the cDNA library.

An oligonucleotide [ACGATGCAAATAACTCAG] corresponding to the N-terminal amino acid sequence of the antigen (see FIG. 1) is synthesized and used to screen the cDNA library for full length clones. The lambda gt11 cDNA library is screened by the plaque hybridization method of Benton and Davis, Science, 196, 180-182 (1977), and Maniatis, using the oligonucleotide probe labelled with $^{32}P$.

The library is plated on 160 mm NZCYM agar plates in NZCYM top agar at $10^4$ p.f.u./plate and incubated at 37° C. for 10-15 hours. Filter replicas of the plates are taken with nitrocellulose filters (BA85, Schleicher and Schuell) and processed according to Maniatis.

Positive lambda gt11 phage clones are picked and replated and rescreened to ensure homogeneity. Purified phage are prepared from several positive clones, and the recombinant phage DNA is isolated and the DNA insert subcloned into a plasmid vector, Bluescript SK (Stratagene).

EXAMPLE 2

Cloning of the 67kDa glycoprotein gene from Theileria piroplasm genomic DNA

*T. parva parva* (Muguga) piroplasms were isolated as previously described in Mack, S. R., 1978, J. Parasit. 64:166-168. For purification of DNA, piroplasms were suspended in 10 ml TNE (10 mM Tris-HCl pH 7.8, 100 mM NaCl, 1 mM EDTA). Sodium dodecylsulphate (SDS) and RNase A (boiled in 10 mM Tris-HCl, 0.1 mM EDTA, pH 8 for 10 min at 93° C.) were added to final concentrations of 0.5% and 100 ug per ml, respectively. The suspension was incubated for 1 hour at 37° C. Proteinase K (BRL, Gettysburg, Md., U.S.A.) was then added to a concentration of 100 ug per ml and the preparation incubated for an additional 2-3 hours at 50° C. The lysate was extracted once with phenol, twice with phenol:chloroform (1:1), and twice with chloroform:isoamyl alcohol (24:1) before precipitation of DNA with two volumes ice cold 100% ethanol. DNA was pelletted at 500×g for 15 min at 4° C., dried at 37° C. and dissolved in sterile TE buffer (10 mM Tris, pH 8.0, 0.1 mM EDTA).

A library of T. parva parva (Muguga) genomic DNA fragments was constructed in the bacteriophage vector lambda gt11 (Promega Biotech) by methods previously described. Young, R. A., et al., 1985, Nature, 316:450-45. Approximately 2 ug of piroplasm DNA were sheared by passage through a 19 gauge needle, 250-300 times, to produce fragments of 3 to 8 kb in size. The DNA was methylated with EcoR I methylase using reaction conditions described by the manufacturer (New England Biolabs, Beverly, Mass., U.S.A.). Treatment with Klenow fragment of DNA polymerase and ligation with EcoR I linkers was carried out as described in Maniatis. The excess DNA was digested twice, for 2 h at 37° C., with 100 units EcoRI, followed, each time, by phenol-chloroform (1:1) extraction and excess linkers removed by passage through a Sephacryl S-300 spin column (Pharmacia, Uppsala, Sweden). The DNA fragments were then mixed with 0.5 ug of dephosphorylated lambda gt11 arms at a 1:2 molar ratio of inserts to arms and ligated using T4 DNA ligase. The recombinant DNA was then packaged into phage particles using commercially available extracts (Promega Biotech) and the resultant phage amplified by plating on E. coli strain Y1O9O. Approximately $1.1\times10^6$ recombinant phage were produced from 0.1 ug insert DNA in a library that contained 85% recombinants.

An oligonucleotide [ACGATGCAAATAACTCAG] corresponding to the N-terminal amino acid sequence of the antigen (FIG. 1) was synthesized and used to screen the genomic DNA library for full length clones. The lambda gt11 genomic DNA library was screened by the plaque hybridization method of Benton and Davis, 1977, Science, 196, 180-182, and Maniatis, using the oligonucleotide probe labelled with $^{32}P$.

The library was plated on 160 mm NZCYM agar plates in NZCYM top agar at $10^4$ p.f.u./plate (10,000 plaque forming units per plate) and incubated at 37° C. for 10-15 hours. Filter replicas of the plates were taken with nitrocellulose filters (BA85, Schleicher and Schuell) and processed according to Maniatis.

Positive lambda gt11 phage clones were picked and replated and rescreened to ensure homogeneity. Purified phage were prepared from several positive clones, and the recombinant phage DNA isolated and the DNA insert subcloned into plasmid vector pUC18 (Pharmacia).

EXAMPLE 3

Production of the 67 kDa Theileria Antigen in Bacterial Cells

The 67 kDA antigen is preferably expressed by manipulating full-length cDNA into expression vectors. However, it is possible to assemble full length expressible sequences from genomic DNA and partial cDNA sequences. Both methods are described below.

Two strategies may be used to express the Theileria antigen. The first expresses the complete gene sequence including the presumptive signal sequence that would not be present in the "mature" sporozoite antigen. The second method expresses sequences encoded by the "mature" gene product.

Figure 3:
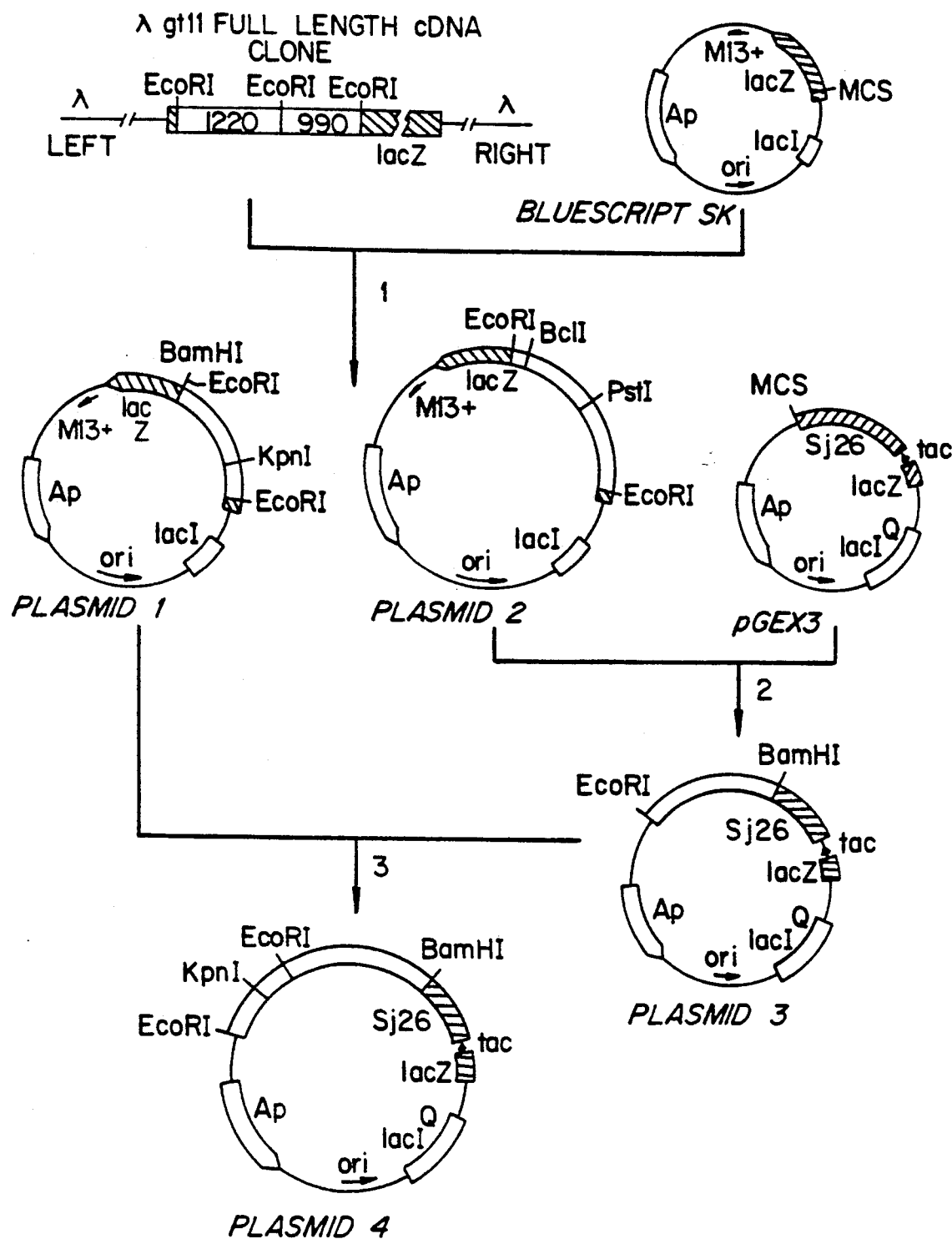
Figure 5:
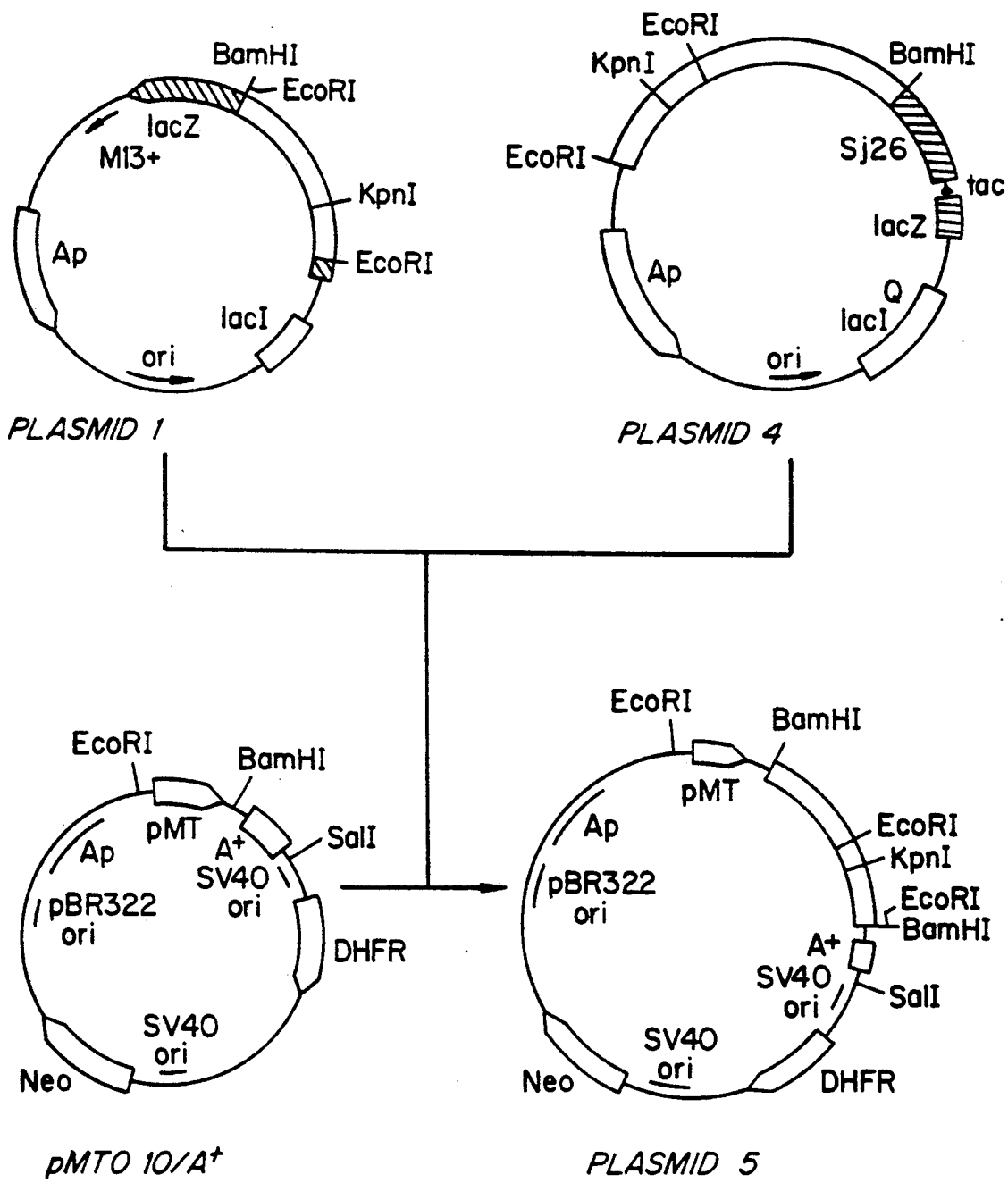

The lambda gt 11 full length cDNA clone, (Example 1) contains two EcoRI fragments, approximately 1220 and 990 bp long (FIG. 3). These are shotgun cloned into the EcoRI site of plasmid Bluescript SK (Stratagene). The Bluescript recombinants (plasmid 1 and 2, see FIG. 3, which contain the 990 bp and 1220 bp DNA fragments, respectively), are used as the source of cDNA in constructing the expression recombinants (FIGS. 3 and 5).

A. Expression of the complete gene product

The gene contains a BclI site 23 nucleotides in from the N-terminal end (FIG. 1). Since BclI digestion is blocked by the dam methylase, plasmid 2 is grown in a methylase-deficient strain of E.coli such as NK5772. Plasmid 2 is prepared from NK5772 and is digested with BclI and a synthetic adaptor is attached to the DNA.

5'
  CGGATCCCGATGCAAATAACT-
  CAGTTTTTGCT 3'

3'
  GCCTAGGGCTACGTTTATTGAGT-
  CAAAAACGACTAG 5'

The adaptor contains a BamHI site at the 5' end. The ligated DNA is digested with BamHI and EcoRI, the 1200 bp DNA is purified and then cloned into pGEX3 (Smith, D. B. & Johnson, K. S., 1988, Gene 67:31–40; Medos Company Pty. Ltd.) to give plasmid 3. The remainder of the gene which is encoded on the 990 EcoRI fragment of plasmid 1 is cloned into the EcoRI site of plasmid 3 and recombinants containing the 990 bp fragment in the correct orientation are isolated. The resulting expression plasmid, plasmid 4, is transformed into an E.coli strain, such as JM109.

The Theileria antigen is purified as described below.

B. Expression of the "mature" gene product

To express the "mature" Theileria 67 kDa antigen, i.e. lacking the signal sequence, step 2 in FIG. 3 is varied as follows. Plasmid 2 is digested with BclI and subjected to limited Bal 31 digestion. BamHI linkers [New England Biolabs #1017] are attached. The DNA is digested with BamHI and EcoRI and the 1200 bp DNA is purified. This DNA is cloned into pGEX3 and the recombinants are sequenced to determine the extent of the Bal 31 deletions. Clones containing deletions ending at nucleotide number 54, 57 and 60 (FIG. 1) are kept and processed.

Plasmid 1 is digested with EcoRI, the 990 bp DNA is purified and cloned into plasmid 3. Recombinants are screened to isolate clones containing the 990 bp EcoRI fragment in the correct orientation, plasmid 4. This plasmid is transformed into an E. coli strain, such as JM109.

To achieve synthesis of the Theileria antigens in E. coli, cultures of JM1109 carrying the expression plasmid are grown in rich medium (e.g., L broth), containing ampicillin to maintain the plasmid, at 30°-37° C. to intermediate cell density. IPTG is then added to induce expression of the recombinant gene from the tac promoter.

The fusion protein is affinity purified from E.coli lysates as described by the manufacturer (Medos Company Pty. Ltd.). This exploits the properties of Sj26, which is encoded by pGEX3 and to which the Theileria antigen is fused. Sj26 is a glutathione-S-transferase which has a high affinity for glutathione. The fusion protein is purified using glutathione-agarose beads and eluted with free glutathione. Pure Theileria antigen is recovered from the fusion protein by cleavage with Factor Xa which cleaves at the fusion site. By passing the cleavage products through the affinity column, Sj26 is retained on the column and pure Theileria antigen is isolated.

C. Assembly of a prokaryotic expression plasmid from partial theileria cDNA sequences and genomic DNA A complete 67 kDa antigen encoding segment was assembled from a genomic DNA clone and from a partial cDNA clone according to FIG. 4. The 2900 bp and 2400 bp EcoRI fragments from the genomic clone and the 800 bp EcoRI fragment from the cDNA clone were shotgun cloned into pUC18 (Pharmacia). The 67 kDa gene spans the two genomic DNA fragments. The recombinant plasmid carrying the 2900 bp insert contains an intron which is located between the PstI and EcoRI sites (see FIG. 4). The partial cDNA clone contains sequences from this EcoRI site to beyond the PstI site. The genomic PstI-EcoRI fragment was replaced with the cDNA PstI-EcoRI fragment thereby removing the intron.

The above plasmid also has a BclI site 23 nucleotides in from the N-terminus of the 67 kDa gene (see FIG. 1). For reasons described earlier, the recombinant plasmid was grown in E. coli strain NK 5772. Purified plasmid was digested with BclI and a synthetic adaptor was ligated to the ends. The adaptor contains a BamHI site at the 5' end and the 22 nucleotides 5' of the BclI site.

5'
  CGGATCCCGATGCAAATAACT-
  CAGTTTTTGCT 3'

3'
  GCCTAGGGCTACGTTTATTGAGT-
  CAAAAACGACTAG 5'

The ligated DNA was digested with BamHI and PstI and the 500 bp DNA was purified. The pUC18 recombinant containing the cDNA insert was digested with PstI and EcoRI and the 600 bp DNA purified. The recovered DNA was ligated to pGEX3 digested with BamHI and EcoRI. The remainder of the 67 kDa gene which is on part of the 2400 bp genomic DNA was cloned into the pGEX3 recombinant to give a construct that expresses the complete 67 kDa gene product.

Figure 4:
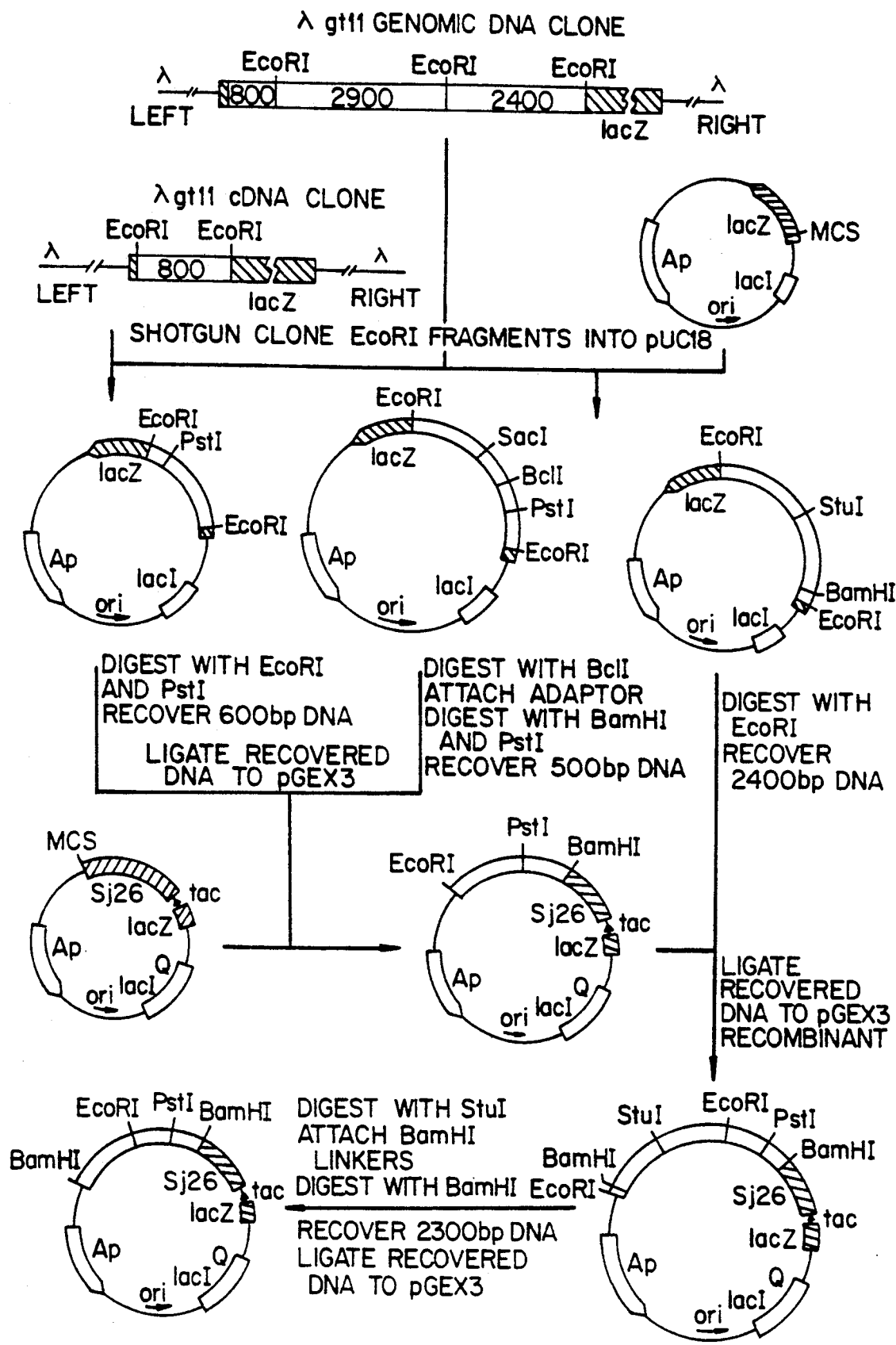

This pGEX3 recombinant, however, contains excess genomic DNA. This extra DNA was deleted by the following procedure. Plasmid DNA was digested with StuI, which cleaves the insert DNA 169 bp downstream of the stop codon of the 67 kDa gene. BamHI linkers were attached to the ends, the ligated DNA was digested with BamHI and the larger 2300 bp DNA fragment was isolated. The recovered DNA was ligated back into pGEX3 digested with BamHI and recombinants containing the insert in the correct orientation were isolated (FIG. 4). This construct also expresses the complete 67 kDa antigen.

For convenience the deposited plasmid, phTpp(mug)-p67sp, provides this 67 kDa antigen encoding segment in a kanamycin resistant plasmid pK19 [Gene, 56:309-312, 1987 and available from CIBA GEIGY, Basle, Switzerland]. The segment is readily excisable using BamHI (FIG. 2). The position of two additional restriction enzyme sites is shown.

EXAMPLE 4

Production of the 67 kd Theileria Antigen in *S. typhimurium*

Two strategies are used to express the 67 kDa antigen in Salmonella. The first involves transformation of Salmonella with an expression plasmid containing the gene. The second method involves introduction of the gene into the chromosome of the Salmonella.

A. Transformation of Salmonella with an expression plasmid carrying the gene encoding the 67 kDa antigen Most *E.coli* cloning vectors will replicate in Salmonella spp. The instability of some of the vectors can be countered to an extent by maintaining a selection on the plasmid in Salmonella by inclusion of antibiotic in the growth medium. The pGEX3 recombinant used to express the Theileria 67 kDa antigen in *E.coli* (see FIGS. 3 and 4) is transformed into avirulent (aroA) *Salmonella typhimurium* and expression of the fusion protein is monitored by Western blotting.

B. Integration of the Gene encoding the 67 kDa antigen into Salmonella

To overcome the problem of plasmid instability in Salmonella, the gene encoding the 67 kDa antigen is inserted into the chromosome of the Salmonella host, using a system based on the his operon of Salmonella, (Hone, D. et al., 1988, A Chromosomal Integration System for Stabilization of Heterologous Genes in Salmonella Based Vaccine Strains, Microbial Pathogenesis, Vol. 5, pp. 407-418. In this case, a hisOG deletion mutation is first introduced into the *S. typhimurium* chromosome, and then replaced by introducing a plasmid containing the complete hisOGD region plus the DNA encoding the 67 kDa antigen. By homologous recombination, the introduced (complete hisOGD region plus DNA encoding the 67 kDa antigen) DNA will replace the hisOG deletion mutation. Recombinants can be selected His+.

The plasmid pADE 172 carries the hisOGD region minus the his regulation sequence (hisO) and part of the hisG gene. This plasmid is transformed into the *S. typhimurium* strain. Strains in which the deleted his region has replaced the chromosomal his sequences are isolated by replica plating on nutrient agar and M9 agar. (Strains carrying a deleted his region are His− and grow on the former but not the latter.) The his strain is then cured of resistant plasmids by standard methods, to allow transformation with another plasmid.

The plasmid pADE 172 contains the complete his OGD sequences. The cDNA encoding the 67 kDa antigen is inserted upstream of hisO, and the recombinant plasmid introduced into the his strain of *S. typhimurium*. Recombinant strains, which are His , are selected on M9 agar, cured of the resident plasmids and tested for expression of the 67 kDa antigen by Western blotting. Confirmation of chromosomal integration is achieved by preparation of chromosomal DNA from recombinant strains and analysis by DNA blotting with the 67 kDa gene.

EXAMPLE 5

Expression of 67 kDa Antigen in Mouse Cells

Figure 6:
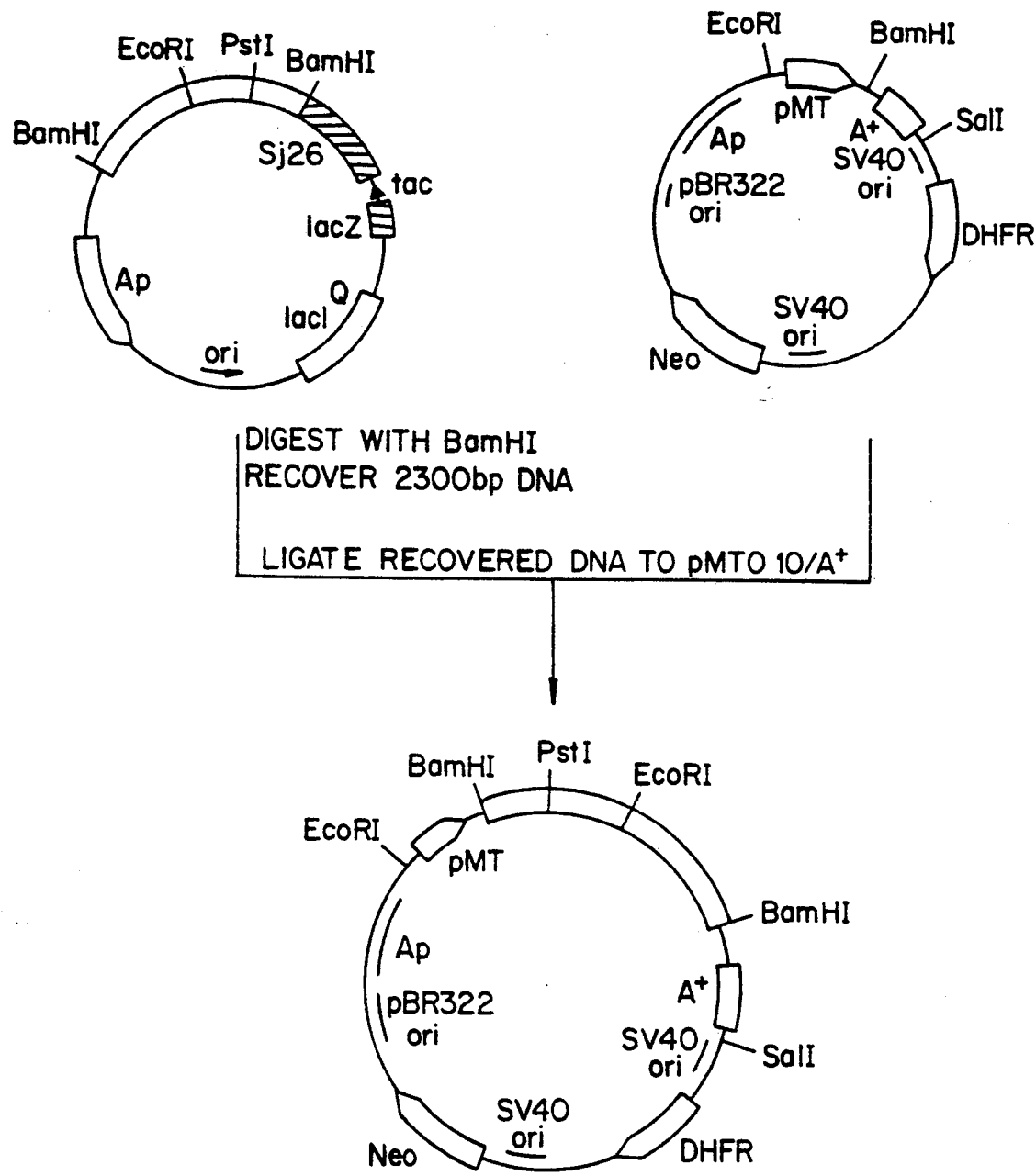

Expression of the 67 kDa antigen in mouse cells can be achieved using either the full length cDNA clone (FIG. 5) or the gene assembled from genomic and cDNA sequences (FIG. 6).

To express the full length cDNA sequence plasmid 1 and plasmid 4, constructed as described in FIG. 3, are digested with BamHI and KpnI and the 600 and 1500 bp inserts which are released are recovered and ligated to pMT010/A+. (Choo, K. H. et al. DNA 5:529-539, 1986; the plasmid was kindly provided by Dr. Choo) digested with BamHI alone. Recombinant plasmid containing both inserts in the correct orientation is isolated and used to transfect mouse cells (FIG. 5).

To express the gene assembled from genomic DNA and cDNA sequences (see FIG. 4) the pGEX3 recombinant or dependent plasmid, phTpp(mug)-p67sp (see FIG. 2), is digested with BamHI and the 2300 bp insert which is released is recovered and cloned into pMT010/A+. Recombinant plasmid containing the insert in the correct orientation is isolated and used to transfect mouse cells (FIG. 6).

Mouse LTK-cells expressing the Theileria antigen are isolated as described by Choo, et al., DNA 5:529-59 (1986). The cells are grown in Dulbecco's Modified Eagle's medium supplemented with 10% foetal bovine serum and the cells are transfected with recombinant plasmid using the calcium phosphate precipitation method. The cells are cultured for 48 hours before selection of G418 (GIBCO Laboratories) resistance. Surviving transformant cells are pooled and subjected to stepwise selection in methotrexate, to co-amplify the cloned Theileria gene. Expression of the Theileria antigen from the metallothionein promoter is increased by the addition of zinc to the growth medium.

EXAMPLE 6

Production of vaccinia viral particles containing gene encoding the 67 kDa antigen The strategy involved in obtaining recombinant vaccinia viral particles encoding the 67 kDa antigen comprises of two steps. The first is to insert the DNA encoding the 67 kDa antigen into a suitable plasmid. The second step involves transfection of the plasmid into mammalian cells which have been infected with vaccinia virus. Incorporation of the DNA encoding the 67 kDa antigen into the genome of the virus occurs by homologous recombination. Positive recombinants are selected, grown in mammalian cell cultures and purified for inoculation into cattle.

a) Construction of plasmid

A plasmid suitable for use in this system is pGS62. Langford, C. J., et al., 1986, Mol. Cell. Biol. 6, 3191-99. The essential features of this plasmid are: i) a multiple cloning site containing BamHI, SmaI and EcoRI sites for insertion of foreign genes, ii) the P7.5 promoter of vaccinia to direct synthesis of the inserted gene and iii) segments of the vaccinia TK gene flanking both ends of the foreign gene to direct homologous recombination of the foreign gene plus TK flanking sequences into the TK gene of vaccinia virus. The BamHI DNA fragment encoding the 67 kDa antigen, constructed either from full length cDNA (FIG. 5) or by assembling a hybrid gene from genomic and cDNA sequences (FIGS. 2 and 4) is inserted into pGS62 at the BamHI site and recombinants containing the insert in the correct orientation are isolated.

b) Production of recombinant virus

The mammalian cells, such as 143 TK⁻ cells are grown as a monolayer to confluency, and inoculated with 0.05 p.f.u. of virus per cell. One microgram of the recombinant plasmid is added to 19 ug of carrier DNA in 1.0 ml HEPES-buffered saline and precipitated by addition of $CaCl_2$ to a final concentration of 125mM, at room temperature for 30 min. Two hours after addition of the virus, the virus inoculum is removed and the monolayer washed twice with medium. The DNA suspension is added to the monolayer and incubated at room temperature. After 30 min, 5ml of medium containing 5% foetal bovine serum is added and the cells are incubated at 37° C. for a further 3.5 hours.

The cells are washed and incubated in medium with 5% foetal bovine serum for 48 hrs. The cells are collected and virus progeny are released by three cycles of freeze thawing. To select for recombinant viruses, 143 TK⁻ cells are inoculated with the virus progeny. One to two hours after addition of the virus, the medium containing the virus inoculum is removed and replaced with medium containing 1% low gelling temperature agarose, 5% foetal bovine serum and 25 ug/ml 5-bromodeoxyuridine. After 48 hrs the monolayer is stained with neutral red to locate virus plaques. These plaques can be selected and amplified for use in a second round of screening. Two cycles of plaquing usually produce a homogeneous viral stock. The presence of the gene encoding the 67 kDa antigen can be confirmed using DNA blotting in which viral DNA is probed with plasmid containing the cDNA encoding the 67 kDa antigen. Expression of the 67 kDa antigen in infected cells can be confirmed by immunoblotting using lysates of virus infected cells and probing with monoclonal antibodies specific for the 67 kDa antigen.

EXAMPLE 7

Immunoreactivity of recombinantly produced 67 kDa antigen in E.coli

Groups of rats have been immunised with two pGEX fusion proteins expressing different regions of the Theileria 67 kDa antigen. Group I received the control Sj26 protein. Group II was immunised with a fusion protein encoding amino acid residues 9-316 (FIG. 1) of the Theileria antigen and group III was immunised with a fusion protein encoding amino acid residues 397-709 of the Theileria antigen.

Each rat was inoculated with 5 ug of protein in complete Freund's antigen as the primary dose. The rats were boosted twice at two week intervals with 5 ug of protein in incomplete Freund's antigen and sacrificed two weeks after the third inoculation.

Sera taken from rats in groups II and III recognise the Theileria 67 kDa antigen on Western blots. Furthermore, the sera from these animals completely neutralise sporozoite infectivity in the in vitro assay system. Control sera from group I rats fail to recognise the Theileria antigen and fail to neutralise sporozoite infectivity.

The above results show that the presence of carbohydrate sidechains on the Theileria antigen are not essential for evoking neutralising antibodies.

Since rats were immunised with two non-overlapping regions of the antigen, there is more than one epitope exposed on the surface of the sporozoite.

Rats have not been immunised with the complete recombinant product, although such a construct is available. The region between residues 316 and 397 were not included in the above experiments.

Plasmid pGEX is a family of three vectors allowing expression of DNA in the three different reading frames. The results described above used pGEX1 and pGEX3.

EXAMPLE 8

Immunization protocol

Areas of Eastern Africa where the disease is prevalent can experience an abundance of ticks after receiving sufficient rainfall. Under these circumstances it is desirable that animals are vaccinated before the rains.

The preferred age of vaccination of calves would be 2 months while vaccination for older stock is done at any time. For both calves and adults the priming dose, composed of 1.0 mg of purified antigen produced by recombinant DNA technology and 3 mg of saponin in 1 ml of saline, would be administered subcutaneously in an area cranial to the prescapular lymph-node, followed by similar booster doses 4 to 8 weeks later. Revaccination should be done semi-annually, particularly for animals under heavy challenge and preferably just before the rains.

What is claimed is:

1. A substantially pure and isolated antigenic polypeptide having the amino acid sequence set forth in FIG. 1 and characterized by inducing immunoprotection against infection by *Theileria parva* in bovine animal species when administered to the animal in an amount effective to induce the immunoprotection.

2. A vaccine for inducing immunoprotection in bovine animal species against infections of *Theileria parva* comprising pharmaceutically acceptable excipients and a substantially pure and isolated antigen having the amino acid sequence set forth in FIG. 1 said antigen present in an amount effective to induce immunoprotection against infection by *Theileria parva* when administered to the animal.

3. A vaccine of claim 2 wherein the antigen is glycosylated.

4. A vaccine of claim 2 wherein the antigen is not glycosylated.

5. A vaccine of claim 2 wherein the animals are cattle.

6. A vaccine of claim 2 wherein the antigen is a recombinant protein.

7. A vaccine of claim 2 wherein the substantially pure and isolated antigen is at least 75% pure.

8. A method for protecting bovine animal species from infection by *Theileria parva* comprising the administration of a vaccine comprising an amount of a substantially pure and isolated antigen having the amino acid sequence set forth in FIG. 1 said amount effective for inducing immunoprotection against infection by *Theileria parva* in the animal.

9. A method of claim 8 wherein the antigen is glycosylated.

10. A method of claim 8 wherein the antigen is not glycosylated.

11. A method of claim 8 wherein the animals are cattle.

12. The method of claim 8 wherein the administering step includes parenteral administration.

13. A method of claim 8 wherein the antigen is a recombinant protein.

14. A method of claim 8 wherein the substantially pure and isolated antigen is at least 75% pure.

* * * * *